(12) United States Patent
Shaimi

(10) Patent No.: US 8,156,788 B2
(45) Date of Patent: Apr. 17, 2012

(54) SUPERCRITICAL-PHASE MIXED CHROMATOGRAPHY METHOD AND INSTALLATION FOR IMPLEMENTING SAME

(75) Inventor: Mohamed Shaimi, Montfavet (FR)

(73) Assignee: PIC Solution, Avignon (FR)

( * ) Notice: Subject to any disclaimer, the term of this patent is extended or adjusted under 35 U.S.C. 154(b) by 795 days.

(21) Appl. No.: 11/885,023

(22) PCT Filed: Feb. 22, 2006

(86) PCT No.: PCT/FR2006/000401
§ 371 (c)(1),
(2), (4) Date: Sep. 15, 2008

(87) PCT Pub. No.: WO2006/090062
PCT Pub. Date: Aug. 31, 2006

(65) Prior Publication Data
US 2009/0049891 A1      Feb. 26, 2009

(30) Foreign Application Priority Data
Feb. 25, 2005   (FR) ..................................... 05 01960

(51) Int. Cl.
*G01N 30/04*      (2006.01)
*G01N 30/72*      (2006.01)
(52) U.S. Cl. ...................... 73/23.36; 73/23.37; 73/23.41; 73/61.52; 73/61.55; 95/82; 95/88; 96/101; 210/198.2; 210/656
(58) Field of Classification Search ................. 73/23.36, 73/23.37, 23.41; 95/82, 88; 96/101
See application file for complete search history.

(56) References Cited

U.S. PATENT DOCUMENTS
4,478,720 A * 10/1984 Perrut ........................... 210/659
(Continued)

FOREIGN PATENT DOCUMENTS
WO   WO 2004/111632      12/2004

OTHER PUBLICATIONS

Zeng, L. et al., "Automated Analytical/Preparative High-Performance Liquid Chromatography-Mass Spectrometry System for the Rapid Characterization and Purification of Compound Libraries", Journal of Chromatography A, vol. 794, No. 1-2, Jan. 23, 1998, pp. 3-13.*

King, J.W. et al., "Analytical Supercritical Fluid Chromatography and Extraction", Supplement and Cumulative Index—Physical Methods of Chemistry Series, 2nd. ed. vol. X, Chapter 1, 1993, pp. 1-86.*

*Primary Examiner* — Daniel Larkin
(74) *Attorney, Agent, or Firm* — Bachman & LaPointe, P.C.

(57) ABSTRACT

A method for the superficial-phase chromatography of a product comprises the steps which are performed continuously in the following order, namely: an operation consisting in pumping a supercritical fluid; and operation consisting of injecting at least one sample of product into at least one chromatography column, a detection operation, and a fraction collection operation. The method comprises at least a first diversion along between an analytical channel and a preparatory channel, which diversion is performed prior to the supercritical fluid pumping operation and the analytical and preparatory channels each including respective supercritical fluid pumping operations. The method is also characterized in that the collection operation is common to both the analytical and preparatory channels. An installation used to implement one such method is described.

13 Claims, 4 Drawing Sheets

U.S. PATENT DOCUMENTS

| | | | |
|---|---|---|---|
| 4,919,595 A * | 4/1990 | Likuski et al. | 417/18 |
| 5,670,054 A * | 9/1997 | Kibbey et al. | 210/656 |
| 6,309,541 B1 * | 10/2001 | Maiefski et al. | 210/198.2 |
| 6,641,783 B1 | 11/2003 | Pidgeon et al. | |
| 7,507,337 B2 * | 3/2009 | Petro et al. | 210/198.2 |
| 2002/0185442 A1 | 12/2002 | Maiefski et al. | |
| 2004/0096986 A1 * | 5/2004 | Klein et al. | 436/514 |
| 2004/0188333 A1 | 9/2004 | Allington et al. | |

* cited by examiner

SUPERCRITICAL-PHASE MIXED CHROMATOGRAPHY METHOD AND INSTALLATION FOR IMPLEMENTING SAME

FIELD OF THE INVENTION

This present invention concerns the area of chromatographic techniques, and more particularly of Supercritical Fluid Chromatography or SFC. In this technique, the mobile phase is composed of a supercritical fluid or a mixture of supercritical fluids.

The invention concerns a method for the supercritical fluid chromatography of a product P, as well as the installation for implementation of such a method.

More precisely, according to a first of its aspects, the invention concerns a method for the supercritical fluid chromatography of a product P that includes, continuously in the following order:
- an operation for the pumping of a supercritical fluid,
- an operation for the injection of at least one sample of the product P in at least one chromatography column,
- an operation for detection, and
- an operation for the collection of fractions.

Such a method is used commonly in SFC. It is used either for analytical or preparatory purposes.

The analytical objective is to identify, qualitatively and/or quantitatively, the solutions present in a product. Quantitative determination involves the application of thermodynamic rules which themselves involve the use of very small quantities of product.

The preparatory objective is different from the analytical objective in that it consists of isolating one or more solutions from a mixture. Thus, in this case, the quantities of product introduced into the method are greater since the aim is to isolate, to a given purity, the maximum quantity of solution per unit time. The operating conditions of the method on the preparatory scale are determined firstly by developing the separation method at the analytical scale.

The attainment of these two objectives currently requires the execution of two chromatography methods, namely an analytical method and then a preparatory method, and using different installations, since the quantities to be processed are significantly different depending on the circumstances, and as a consequence, the instruments constituting the installations are of different dimensions.

SUMMARY OF THE INVENTION

This present invention therefore has as its objective to provide a supercritical fluid chromatography method that is free of these limitations.

To this end, the method of the invention, which also conforms to the generic definition provided in the above preamble, is essentially characterised in that it includes at least one first routing between an analytical path and a preparatory path, where the said first routing occurs prior to supercritical fluid pumping operation, and where the said analytical and preparatory paths each includes its own supercritical fluid pumping and injection operations, and in that the collection operation is common to the analytical and preparatory paths.

In general, an eluent constitutes the mobile phase of a chromatography operation. According to the invention, the mobile phase is based upon a fluid that is chosen from any fluid that is compatible with a supercritical fluid chromatography application. In what follows, such a fluid is called the supercritical fluid, even if, in certain conditions of pressure and temperature, the fluid is not in a supercritical state in the strict sense of the term.

To this supercritical fluid, can be added a liquid solvent or a mixture of liquid solvents which will be called a modifier. The supercritical-modifier fluid mixture constitutes the eluent.

The invention therefore has the advantage of providing a mixed SFC method, which, by means of a single installation, can be used alternately to perform analytical chromatography and preparatory chromatography.

According to a first preferred embodiment, an operation for the pumping of a modifier takes placed in parallel with a supercritical fluid pumping operation, and the pumped streams converge so as to effect the addition of the modifier to the supercritical fluid, toward a main path that is common to the analytical and preparatory paths, upstream of a second routing toward the respective injection operations of the analytical path and the preparatory path.

The modifier can be an organic solvent which is added in order to modify the polarity of the mobile phase. According to the invention, the supercritical-modifier fluid mixture constitutes the mobile phase for supercritical fluid chromatography.

According to a second preferred embodiment of the invention, an operation for the pumping of a modifier and the addition of the latter to the supercritical fluid takes place upstream of the first routing. In this case, supercritical fluid pumping operation consists not only of pumping the supercritical fluid but also mixing it with the modifier.

The detection operation is accomplished by ultraviolet spectroscopy for example.

Preferably, the method of the invention includes an operation for controlling the temperature of the eluent between the pumping operations and the injection operations.

In an advantageous manner, the collection operation includes an operation upstream for regulation of the pressure.

According to the invention, the supercritical fluid can be carbon dioxide $CO_2$, for example.

Another aspect of the invention is an installation for the supercritical fluid chromatography of a product P, which includes the following parts:
- two supercritical fluid pumps to pump the said fluid, mounted in parallel, and only one of which is operational during operation of the installation,
- a first routing valve upstream of the said pumps, which is operated so that the supercritical fluid is allowed to flow toward the operational pump,
- two systems for the injection of at least one sample of the product P into at least two respective chromatography columns, the said systems being mounted in parallel downstream of the supercritical fluid and modifier pumps and, downstream of the columns,
- a detection appliance, and
- a fraction collection system.

In an advantageous manner, a modifier pump equipped with an interchangeable head can be placed just upstream of the first routing valve or just upstream of a second routing valve placed downstream of the supercritical fluid pumps.

According to a more particularly preferred embodiment, the modifier pump is a low-pressure pump placed upstream of the first routing valve, and the alternately operational supercritical fluid pumps are high-pressure pumps.

Preferably, the installation according to the invention includes a device for computer control of the different parts of the said installation.

The installation according to the invention includes, for example, a heat exchanger placed downstream of the supercritical fluid and modifier pumps and upstream of the injection systems.

The two supercritical fluid pumps preferably have respective flow capacities with a ratio of at least 2.5.

Preferably, the installation of the invention includes a back-pressure regulator downstream of the detection appliance and upstream of the collection system.

According to the invention, the detection appliance can be an ultraviolet spectrophotometer, and can include either two measuring cells each mounted in parallel after the respective chromatography columns, or two interchangeable cells just downstream of a third routing valve placed after the chromatography columns.

BRIEF DESCRIPTION OF THE DRAWINGS

Other advantages and particular features of the invention will appear on reading the detailed description which is provided below by way of guidance and in no way limiting, and with reference to the appended drawings in which.

DETAILED DESCRIPTION OF THE PREFERRED EMBODIMENT(S)

Figure 1:
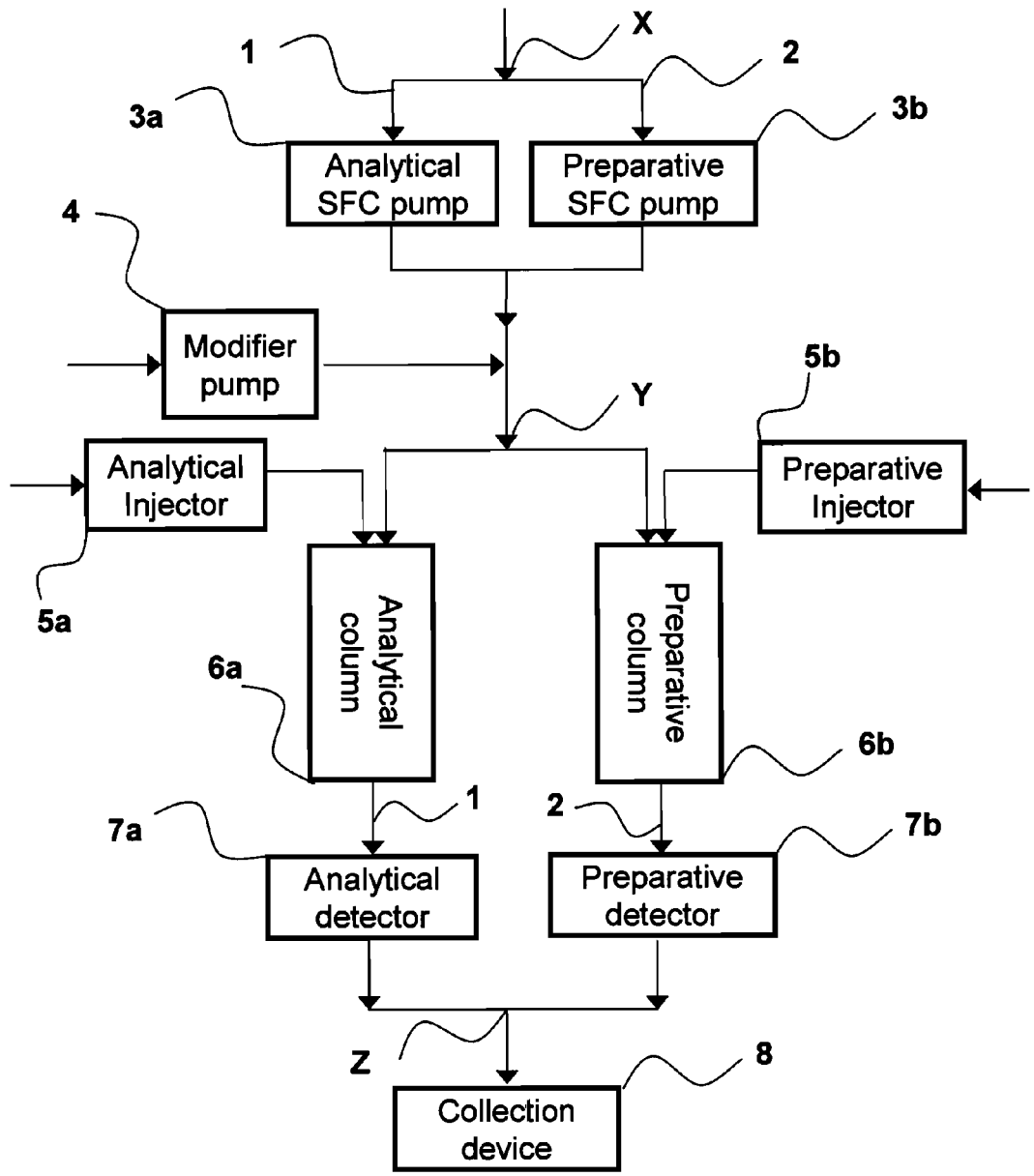
FIG. 1 schematically represents a first embodiment of the method according to the invention.
Figure 2:
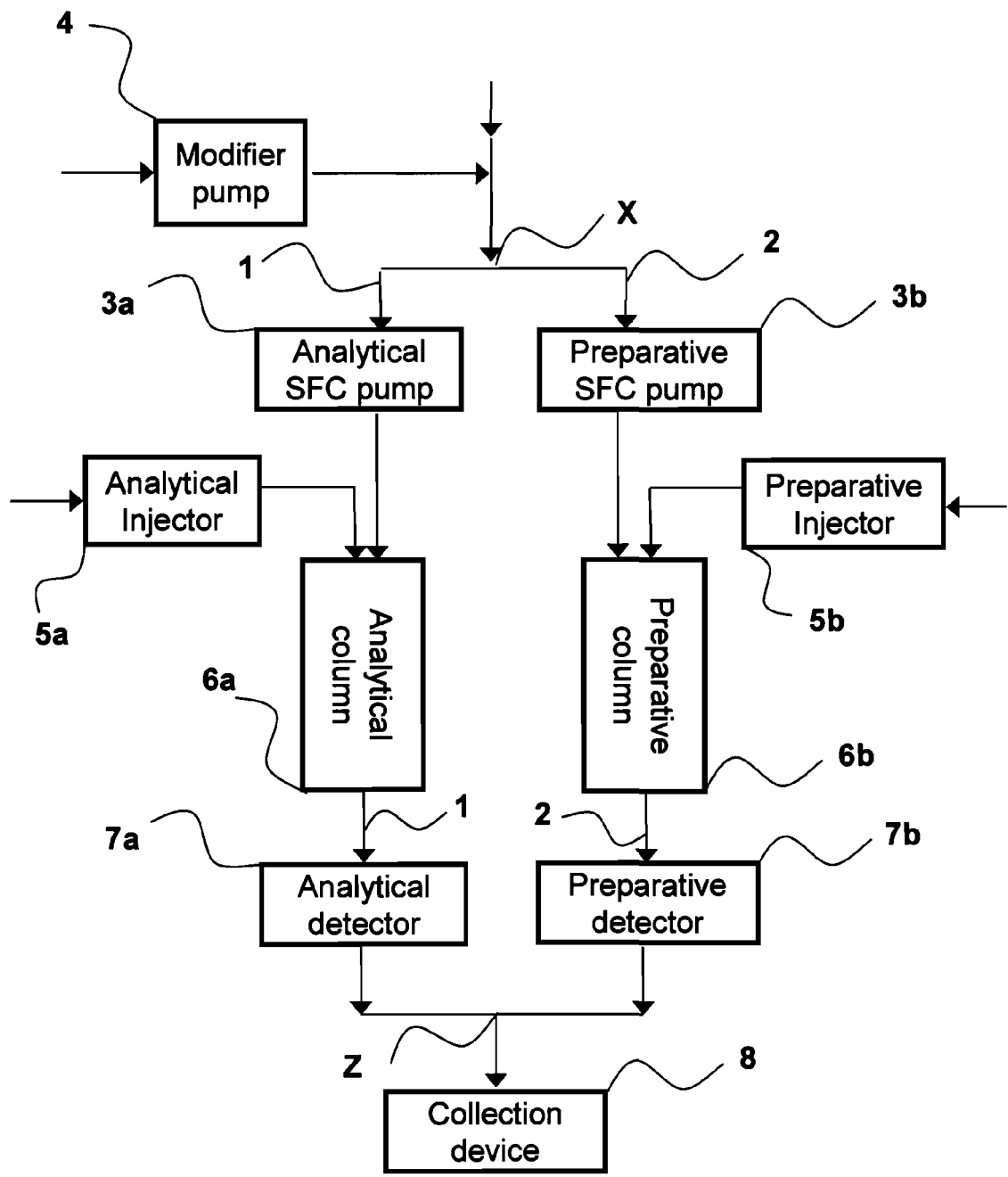
FIG. 2 schematically represents a second embodiment of the method according to the invention.

FIGS. 1 and 2 illustrate the method according to the invention, and more particularly two preferred embodiments.

According to the invention, the method for supercritical fluid chromatography or SFC of a product P includes, continuously and in the order listed, the operations of pumping 3 of a supercritical fluid, injection 5 of at least one sample into at least one chromatography column 6, detection 7 and fraction collection 8.

The supercritical fluid can be any fluid that is compatible with supercritical fluid chromatography. As an example, the supercritical fluid can be carbon dioxide $CO_2$.

Before the pumping operation 3, the supercritical fluid can be subjected to an operation for controlling its temperature, and more precisely a cooling operation.

The method can also include a pumping operation 4, 4', for a modifier. This operation can take place between the operations for pumping 3 and injection 5 of the supercritical fluid, or upstream of the pumping operation 3.

According to the invention, the modifier can be an alcohol, such as methanol, ethanol or isopropanol, or any other organic solvent or mixture of organic solvents.

An analytical path 1 or a preparatory path 2 can be taken in accordance with the routing that is effected in X and Y.

The method via the analytical path has a lower flow in relation to the method via the preparatory path.

In FIG. 1, the pumping 4 of the modifier takes place between the pumping operation 3 of the supercritical fluid and the injection operation 5. Thus, the flow of supercritical fluid and modifier converge upstream of the routing in Y.

In this first embodiment of the invention, a first routing takes place in X between a pumping 3a of supercritical fluid at an analytical rate and a pumping 3b of supercritical fluid at a higher rate for the preparatory mode. A second routing takes place in Y between an analytical injection operation 5a and a preparatory injection operation 5b.

In FIG. 2, the pumping 4' of the modifier takes place upstream of the routing in X. Thus, the flow of supercritical fluid and modifier converge upstream of the routing in X. In this case, the routing in Y is no longer necessary.

According to the invention, in general, the analytical 1 and preparatory 2 paths each includes a pumping operation 3a, 3b and an injection operation 5a, 5b in at least one chromatography column 6a, 6b.

The detection operation 7 can be common to the two paths upstream of a Z routing, and can consist of two detection operations 7a, 7b in the analytical path 1 and the preparatory path 2, respectively.

Preferably, in order to effect the detection operation 7, two cells are used, namely an analytical cell 7a in the analytical path 1 and a preparatory cell 7b in the preparatory path 2. According to the path selected, the cell is connected by optical fibre to a single ultra-violet spectrophotometer detector.

Preferably, detection 7 is accomplished by ultraviolet spectroscopy. Nevertheless, it is possible to envisage any detection technique that is compatible with the solution to be detected and with the operating conditions (nature of the eluent, etc.). Thus, by way of an example, it would be possible to use mass detection, infrared and evaporative light scattering detection (ELSD).

The final operation for collection 8 of the separated fractions by passage in the chromatography column or columns 6a, 6b is common to the analytical 1 and preparatory 2 paths.

This collection operation 8 consists conventionally of separating, in a first stage, each fraction of the eluent, that is of the supercritical-modifier fluid mixture, and then of storing each fraction, pure or in solution, in the modifier after removal of the supercritical fluid previously evaporated, before their drainage for use.

According to a particular method of implementation of the invention, the collection operation 8 includes, upstream, a first pressure regulation operation and possibly a second pressure regulation operation.

Figure 3:
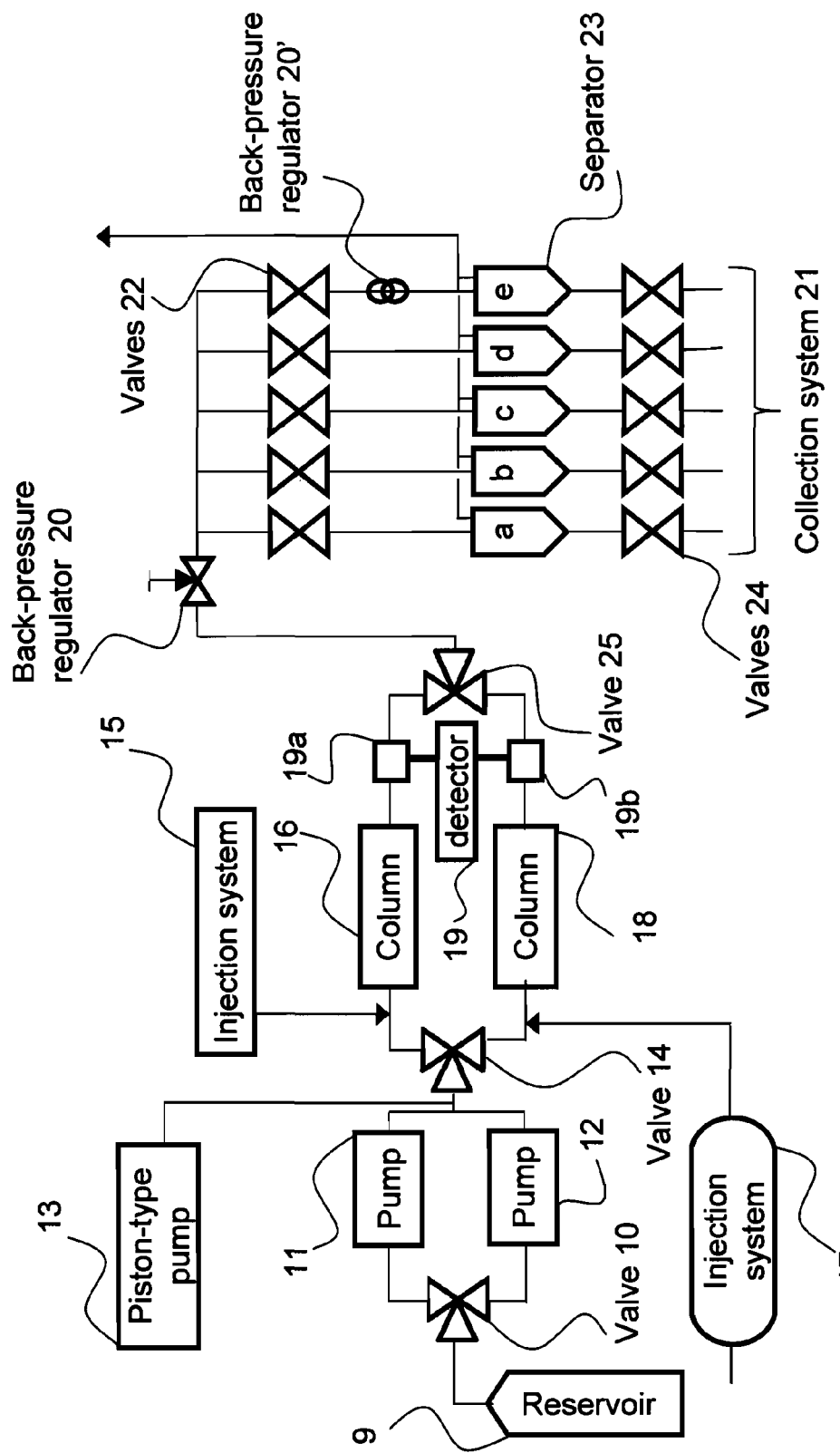
FIG. 3 schematically represents a first embodiment of the installation according to the invention.
Figure 4:
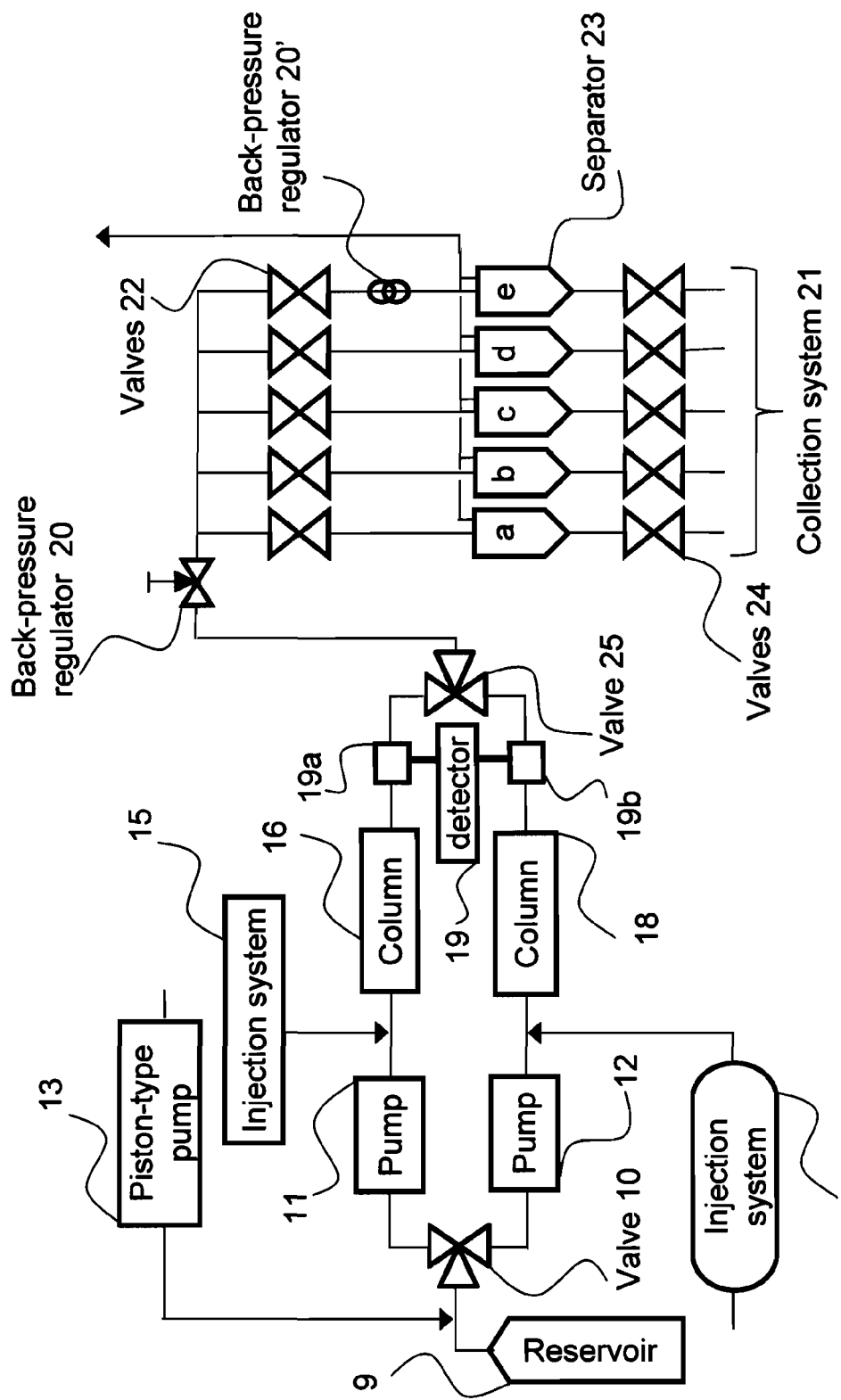
FIG. 4 schematically represents a second embodiment of the installation according to the invention.

FIGS. 3 and 4 illustrate the installation for the supercritical fluid chromatography or SFC of a product P, and more particularly two preferred embodiments of such an installation.

According to the invention, a reservoir 9 of supercritical fluid, such as $CO_2$, is connected either to a low-flow supercritical fluid pump 11 or to higher-flow supercritical fluid pump 12, depending on the position of the first valve 10.

The low flow characterises operation in analytical mode while the higher flow characterises operation in preparatory mode.

The invention has the advantage of proposing an installation that is free of pressure drop, dead volume and detection peak shape problems that can be due to the flow rate differences between the two operating modes if they were to use the same path. The inside diameters of the tubes of the installation, the dead volume, and the regime characteristics (turbulent or laminar) are chosen separately for each of the analytical and preparatory modes.

The low flow pump 11, of the analytical mode, has a maximum flow of 20 ml/min, and preferably a flow that is less than 10 ml/min, for a pressure of 300 bar. Pump 12 has a higher flow than pump 11.

The ratio between the respective flow capacities of the two eluent pumps is at least 2.5, and preferably at least 3, and even more preferably at least 4.

In both modes, the carbon dioxide $CO_2$, for example, is condensed and then pumped and pressurised to working pressure.

The addition of the modifier is effected by a piston-type pump 13, 13' with a variable head. The modifier can be adjusted between 0 and 100%, in quantity of modifier, in relation to the total flow, in both the analytical mode and preparatory mode. The change from one mode to the other is effected automatically by the computer control software and in terms of manual operation requires only changing the pump head, this being an easy and rapid operation.

An alternative to changing the head of the pump 13, 13' is to use two modifier pumps, one pump for each path.

The temperature of the eluent is controlled by means of a heat exchanger before entering into the column 16, 18. The unit thus offers the ability to operate at a temperature below ambient temperature, which in certain cases can improve selectivity and therefore productivity.

A reservoir 9 changing system can automatically switch from an empty reservoir to a full reservoir allowing the installation to function without interruption.

According to different embodiments of the invention, the modifier pump 13 can be located downstream of the supercritical fluid pumps 11, 12, as shown in FIG. 3, or upstream of the first valve 10, as shown in FIG. 4.

In the case illustrated in FIG. 3, a second valve 14 is placed downstream of the supercritical fluid 11, 12 and modifier 13 pumps, and therefore receives a flow composed of supercritical fluid and modifier.

This second valve 14 directs the flow that it receives either toward a system 15 for injection into at least one chromatography column 16 for the analytical mode, or toward a system 17 for injection into at least one chromatography column 18 for the preparatory mode.

In the case illustrated in FIG. 4, the flows emerging from the supercritical fluid pumps 11, 12 are directed respectively toward the system 15 for injection into at least one chromatography column 16 for the analytical mode and toward the system 17 for injection into at least one chromatography column 18 for the preparatory mode.

The injection system 15 in analytical mode can be composed of an automatic sampler. The automatic sampler offers all the advantages of an automatic injection system, such as the execution of single and repeated injections, programmed injections of the same sample or of a different sample, and reproducibility. This allows the operator to rapidly and efficiently install a separation method for a rapid changeover to preparatory mode.

In preparatory mode, a particular injection system 17 allows the operator to execute the manual injections using a syringe or automatic injections with a pump. This operation can be effected without disconnecting any equipment.

Manual injection is useful to test the efficiency of the column and/or for the separation of fractions when the quantity of sample is small and the required injections are small. For a small volume of sample, using the injection pump can result in loss of the sample, since a minimum volume is necessary just to fill the tubes of the installation. In this case, manual injection is both convenient and suitable. Nevertheless, when multiple injections are required, then automatic injection using a pump is best. In both injection systems, the loop size of the product to be injected can be adjusted.

The injection systems 15, 17 are designed with a very small dead volume so that they can be cleaned easily and rapidly between the different uses of the installation.

The injection systems 15, 17 are designed to operate with columns with an inside diameter of between 4.6 mm and 1 cm for the analytical mode, and with columns of larger size, with an inside diameter equal to or greater than 1 cm, for the preparatory mode. The choice of the inside diameter of the columns depends on the column length and on the size of the particles that it has to contain. In the case where the installation has several type 16 columns and/or several type 18 columns, one or two column-selection valves are available to allow column switching during the operation of the installation. The analytical 16 and preparatory 18 columns can each be six in number, for example.

The detector 19 represented in FIGS. 3 and 4, upstream of a routing valve 25 placed at the point of convergence of the analytical and preparatory paths upstream of the collection system 21, operating in the ultraviolet for example, can advantageously be common to the two modes. Two separate UV cells, an analytical cell 19a and a preparatory cell 19b, of different size, can be used in order to obtain an optimal detection peak profile, whatever the operating mode.

According to another embodiment of the invention (not shown), the detector can be installed after the routing valve 25 and can include either a single measuring cell or two measuring cells which are then interchangeable depending on the operating mode, analytical or preparatory, of the installation.

The column output pressure is set in using back-pressure regulator 20, which is common to the two operating modes of the installation.

An additional back-pressure regulator 20' can be added in analytical mode, at low flow, to control back-pressure in the collection line devoted to the analytical mode, allowing the main back-pressure regulator 20 to control the column output pressure. This solution can be employed when the flow difference between the two modes is so great that a single back-pressure regulator is not sufficient to control the column output pressure for the two modes.

The dead volume is reduced to the minimum in order to avoid post-column re-mixing that would affect the final purity of the isolated fractions.

The collection system can include five valves 22a,b,c,d,e. In FIGS. 3 and 4, valve 22e is reserved to the analytical mode and valves 22a,b,c, and are reserved to the preparatory mode.

In preparatory mode, the different fractions obtained at the output of the column or columns 18 are divided between valve 22a for the waste fractions and valves 22b,c, and d for the useful fractions, one for each enantiomer for example, and one for the mixture of the two enantiomers or mean fraction.

The addition of supplementary valves can be envisaged for fractions of additional interest.

Here, the dead volume is again reduced to the minimum in order to avoid a re-mixing of the fractions.

The fractions can be collected on the basis of a time criterion or on the basis of threshold W, measured at detector 19.

Separators 23a,b,c,d,e are used to separate the $CO_2$ of each fraction, dilute or not, in the modifier. The purified fractions can then be reassembled easily.

Each purified fraction is stored in a medium-pressure receptacle fitted with a valve 24 for periodic draining in order to retrieve the fraction.

In an advantageous manner, the installation can be managed by a control application which allows selection between the analytical mode and the preparatory mode.

Using a parameter identification system PID, visible on a screen, the different parts of the installation according to the invention, such as the valves, the pumps and the pressure regulators, can be operated by a simple click during operation of the installation. Control of the method can be effected directly by the operator from the PID system or automatically by loading a method.

The operator selects the analytical mode in order to develop methods for a given separation. A method containing all the separation parameters (flow, modifier rate, pressure, temperature, choice of column, etc.) can be created by the operator. Likewise, a sequence containing several different methods can also be created by the operator and executed by the software in an automatic manner without the intervention of the operator, so as to identify the most suitable separation method more rapidly. The operator is also able to control the installation from the PID system when not many injections are necessary in order to develop a separation method.

Preparatory methods are created by the operator for each separation and contain all of the necessary parameters for production, namely total flow, modifier rate, pressure, temperature, injection quantity, cycle time, number of injections and collection parameters. Methods are recorded under appropriate names and can be loaded for likely future separations.

The operator can also use the PTD system manually when small quantities of product P have to be separated, and for example, he is able to effect one to four preparatory injections using manual injection with the syringe.

At the end of each use of the installation for the production of a purified product P', a rinsing method can be employed to clean the injection system and the collection system in order to prepare the installation for the following use.

Parameters such as flow, pressure, temperature, the signal from the detectors, the status of the collection valves, applicable to a specific method, can be shown during the separation. The separation report, containing chromatograms, recorded under specific names, as well as the operating conditions, can be printed for the laboratory record books.

The software can also operate alarm systems, concerning the high-pressure limit and collection time for example, and as a consequence is able to control operation of the installation by adapting the value of the parameters concerned.

What is claimed is:

1. A method for the supercritical fluid chromatography of a product, comprising the steps of:
    performing a pumping operation for a supercritical fluid,
    performing at least one first routing between an analytical path and preparatory path, where the at least one first routing occurs prior to the operation for pumping the supercritical fluid, and where the said analytical and preparatory paths each includes an analytical and preparative column, respectively, and its own supercritical fluid pumping and injection operations, each adjusted according to whether the chromatography is analytical or preparative,
    performing an injection operation for at least one sample of the product in one of the analytical or preparative chromatography column,
    performing an operation for detection,
    performing a regulation of the pressure of the system downstream of the detection,
    performing operation for the collection of fractions, and wherein the regulation of pressure and the collection operation is common to the analytical and preparatory paths.

2. The method according to claim 1, further comprising performing a pumping operation of a modifier in parallel with the pumping operation of the supercritical fluid, and the pumped streams converging to effect the addition of the modifier to the supercritical fluid, toward a main path that is common to the analytical and preparatory paths, upstream of a second routing toward the respective injection operations for the analytical path and the preparatory path.

3. The method according to claim 1, further comprising performing a pumping operation of a modifier, and addition of the modifier to the supercritical fluid taking place upstream of the first routing.

4. The method according to claim 1, wherein the detection operation step is performed by ultraviolet spectroscopy.

5. The method according to claim 1, further comprising performing an operation for controlling the temperature of the supercritical fluid between the pumping operations and the injection operation.

6. The method according to claim 1, wherein the supercritical fluid is carbon dioxide $CO_2$.

7. An installation for the supercritical fluid chromatography of a product, comprising:
    two supercritical fluid pumps, one of analytical capacity, the other of preparative capacity, mounted in parallel, only one of which is operational during operation of the installation,
    a first routing valve upstream of said pumps, which is operated so that a supercritical fluid is allowed to flow toward the operational pump,
    two systems for the injection of at least one sample of the product into at least two chromatography columns respectively, the injection system and the column size being chosen according to whether the path is for analytical or preparative chromatography, with the systems being mounted in parallel downstream of the pumps and upstream of the columns,
    a tubing of narrow diameter to minimize spreading for the chromatographic bands in the analytical path and of wider diameter to minimize the operation pressure drop in the preparative path,
    a second routing valve downstream of the columns,
    a detection appliance mounted downstream of said second routing valve,
    a system for the collection of fractions, and
    a back pressure regulator, which is common to the analytical and preparatory paths, and mounted downstream of the detection device but upstream of the system for collection of fractions.

8. The installation according to claim 7, in which a modifier pump equipped with an interchangeable head is placed just upstream of the first routing valve or just upstream of a second routing valve placed downstream of the supercritical fluid pumps.

9. The installation according to claim 8, in which the modifier pump is a low-pressure pump placed upstream of the first routing valve, and in which the supercritical fluid pumps are high-pressure pumps.

10. The installation according to claim 7, further comprising a device for computer control of the different parts of the said installation.

11. The installation according to claim 7, further comprising a heat exchanger placed downstream of the supercritical pumps and upstream of the injection systems.

12. The installation according to claim 7, wherein the supercritical fluid pumps have respective flow capacities with a ratio of at least 2.5.

13. The installation according to claim 7, wherein the detection appliance is an ultraviolet spectrophotometer and includes either two measuring cells mounted in parallel, each after respective chromatography columns, or two interchangeable cells just downstream of a third routing valve placed after the chromatography columns.

* * * * *